United States Patent [19]

Fujii et al.

[11] 4,258,193

[45] Mar. 24, 1981

[54] DISULFIDE DERIVATIVES HAVING S—S EXCHANGE REACTIVITY

[75] Inventors: Tadashiro Fujii, Mishima; Nobuaki Nakagawa; Kikuo Kotani, both of Shizuoka, all of Japan

[73] Assignee: Toyo Jozo Kabushiki Kaisha, Shizuoka, Japan

[21] Appl. No.: 57,502

[22] Filed: Jul. 13, 1979

[30] Foreign Application Priority Data

Jul. 13, 1978 [JP] Japan .................................. 53-85900

[51] Int. Cl.³ .................. C07D 405/12; C07D 211/72; C07D 277/78; C07C 103/52
[52] U.S. Cl. ..................................... 546/281; 546/294; 548/166; 260/112.5 R
[58] Field of Search ........................ 546/278, 281, 294; 548/166; 260/112.5 R

[56] References Cited

U.S. PATENT DOCUMENTS 3,150,130  9/1964  Hardman .............................. 548/166

OTHER PUBLICATIONS

Biochem. J., 1973, 133, pp. 573–584, "Prep. of Fully Active Papain from Dried Papaya Latex", Brocklehurst, et al.

T. King, et al., "Prep. of Prot. Conjugates via Intermolecular Disulfide Bond", Biochemistry, vol. 17, No. 8, 1978, pp. 1499–1506.

Primary Examiner—Henry R. Jiles
Assistant Examiner—Robert C. Whittenbaugh
Attorney, Agent, or Firm—Young & Thompson

[57] ABSTRACT

A disulfide derivative, having S—S exchange reactivity, of the formula

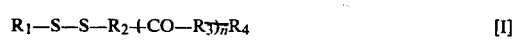

$$R_1-S-S-R_2+CO-R_3\!\!\mid_{\overline{n}}\!\!R_4 \qquad [I]$$

wherein $R_1$ is 2-benzothiazolyl or 2-pyridyl-N-oxide, $R_2$ is alkylene having optionally free or protected functional groups, $R_3$ is the carboxyl residue of an amino acid or lower polypeptide, $R_4$ is carboxyl or a reactive derivative thereof or protected carboxyl or imidate, and n is 0 or 1.

4 Claims, 1 Drawing Figure

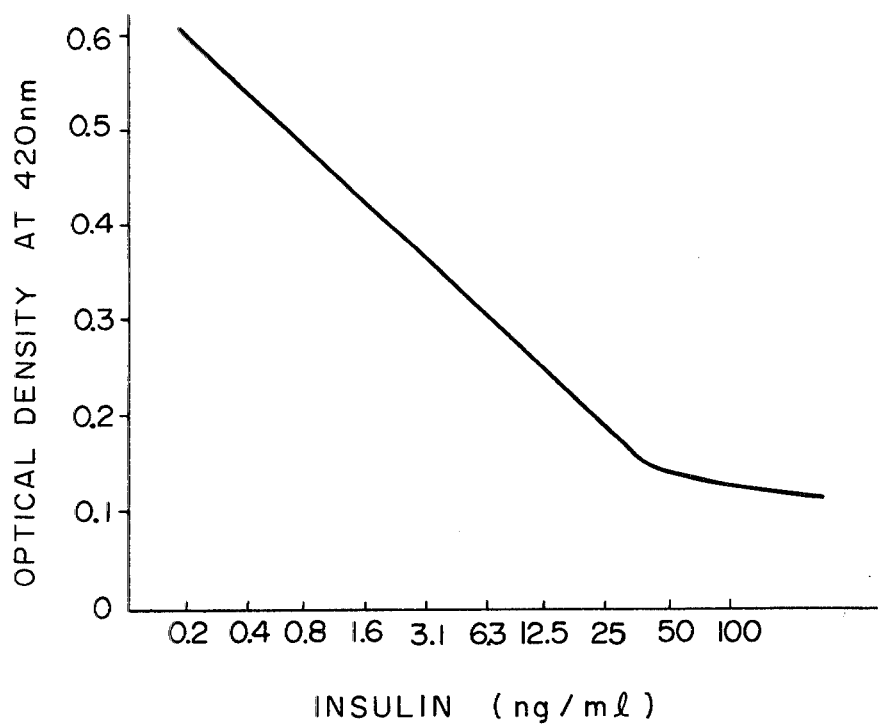

DISULFIDE DERIVATIVES HAVING S—S EXCHANGE REACTIVITY

This invention relates to novel disulfide derivatives, having S—S exchange reactivity, of the formula $$R_1-S-S-R_2+CO-R_3\}_n R_4 \quad [I]$$

wherein $R_1$ is 2-benzothiazolyl or 2-pyridyl-N-oxide, $R_2$ is alkylene having optionally free or protected functional groups, $R_3$ is the carboxyl residue of an amino acid or lower polypeptide, $R_4$ is carboxyl or a reactive derivative thereof or protected carboxyl or imidate, and n is 0 or 1.

The novel disulfide derivatives are useful reagents having S—S exchange reactivity and reactive derivatives of the carboxyl groups thereof can be used as thiol group introducing reagents.

Heretofore, disulfide derivatives having S—S exchange reactivity for compounds having thiol groups have been known and used for covalent chromatography. [Biochem. J., 133, 573–584 (1973); "Affinity Chromatography Practice and Application," pps. 64–65 (1976) K. K. Kodansha, in Japanese; Farmacia, 14(1), 47–52 (1978)]. Some disulfide derivatives are used, based on their S—S exchange reactivity, as cross-linking reagents for reactions between proteins having thiol groups and proteins having amino groups. [Biochem., 17(8), 1499–1506 (1978)].

However, the S—S exchange reaction rate of the known disulfide derivatives is quite slow, and hence the compounds are disadvantageous for this reason.

We have found that novel disulfide derivatives of the formula [I]

$$R_1-S-S-R_2(CO-R_3\}_n R_4 \quad [I]$$

wherein $R_1$, $R_2$, $R_3$, $R_4$ and n have the same meanings hereinabove, are especially useful compounds in that when $R_1$ is 2-benzothiazolyl or 2-pyridyl-N-oxide and $R_2$ is alkylene, the S—S exchange reaction proceeds 2–10 times more rapidly than is ordinarily the case with known compounds.

In the disulfide compounds of formula [I] (hereinafter designated as disulfide derivative [I]), $R_1$ is straight or branched chain alkylene optionally having free or protected functional groups wherein the said functional groups are for example amino or carboxyl, and $R_3$ is a spacer group without detrimental effect on S—S exchange reactivity, for example a carboxyl residual group of an amino acid or a lower polypeptide. Examples of amino acids are known α-amino acids and ω-amino acids. Examples of lower polypeptide are peptides constituted by 2–5 amino acids. $R_4$ is carboxyl or its functional derivative such as active ester or acid halide, or protected carboxyl or imidate, and n is 0 or 1.

Examples of disulfide derivatives of the present invention are illustrated in Table 1. Since disulfide derivative [I] has as $R_1$ benzothiazolyl or pyridyl-N-oxide and $R_2$ is alkylene, S—S exchange reactivity is extremely advantageous.

TABLE 1.

$R_1-S-S-R_2+CO-R_3\}_n R_4$

| $R_1$ | $R_2$ | $R_3$ | n | $R_4$ |
|---|---|---|---|---|
| 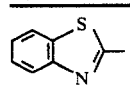 | —CH$_2$—<br>—CH$_2$.CH$_2$—<br>—CH—<br>$\quad$\|<br>$\quad$CH$_3$ | —NHCH$_2$(CH$_2$)$_3$.CH$_2$—<br>—NH.CH$_2$—<br><br>—NHCH$_2$CONHCH$_2$— | 0<br><br><br>1 | —COOH<br><br>—COO—N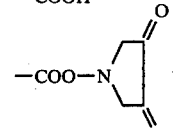 |
| 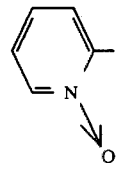 | —CH$_2$—CH—<br>$\qquad$\|<br>$\qquad$NH$_2$ | —NHCH$_2$CONHCH—<br>$\qquad\qquad$\|<br>$\qquad\qquad$CH$_3$ | | —COO——NO$_2$<br><br>—COOCH$_2$— |
| | CH$_3$<br>\|<br>—C——CH—<br>\| \|<br>CH$_3$ NH$_2$ | | | —COCl |
| | —CH—<br>\|<br>CH$_2$COOH | | | —COBr |
| | —CH—CH$_2$—<br>\|<br>COOH | | | NH$_2$Cl<br>\|\|<br>—C.OCH$_3$ |
| | —CH$_2$—CH—<br>$\qquad$\|<br>$\quad$NHCOCH$_2$CH$_2$—CH—NH$_2$<br>$\qquad\qquad\qquad\qquad$\|<br>$\qquad\qquad\qquad\qquad$COOH | | | |

Examples of the synthesis of disulfide derivative [I] are as follows:

$$R_1-S-S-R_2 \quad [II]$$

$$HS-R_2+CO-R_3\}_n R_5 \quad [III]$$

$$R_1-S-S-R_2+CO-R_3\}_n R_5 \quad [IV]$$

$$R_1-S-S-R_2+CO-R_3\}_n R_4 \quad [I]$$

wherein $R_5$ is the same as $R_4$ or is a group which can be changed to an imidate group, and $R_1$, $R_2$, $R_3$, $R_4$ and n have the same meanings hereinbefore.

Examples of $R_1$—S—S—$R_1$ of formula [II] are 2,2'-dithio-bis-(benzothiazol) and 2,2'-dithio-bis-(pyridin-N-oxide).

Examples of HS—$R_2$-(-CO—$R_3$-)$_n$-$R_5$ of formula [III] are thiocarboxylic acid or its carboxylic acid derivatives which react with compounds of formula [II], for example functional derivatives or protective derivatives of active esters or acid halides, and compounds having nitrile groups which can be changed to imidate groups such as thio-nitrile. Examples are thioglycolic acid, β-mercaptopropionic acid, thiolactic acid (α-mercaptopropionic acid), thiomalic acid, cysteine, penicillamine, glutathione, condensation products of β-mercaptopropionic acid and ε-aminocaproic acid and β-mercaptopropionitrile or its carboxylic acid derivatives. In the above compounds, functional groups in a molecule such as amino or carboxyl can be, if required, protected by acid formation using organic or inorganic acids or bases, or protected by known protective groups. These protective groups are known in the field of peptide synthesis and can easily be removed by known methods such as hydrolysis, acid decomposition, reduction, aminolysis or hydrazinolysis.

Examples of protective groups for amino groups are acyl groups such as formyl, trifluoroacetyl, phtharoyl, benzenesulfonyl, p-toluenesulfonyl, o-nitrophenylsulfenyl or 2,4-dinotrophenylsulfenyl, aralkyl groups such as benzyl, diphenylmethyl or triphenylmethyl (these groups can be optionally substituted by lower alkoxy groups such as o-methoxy or p-methoxy groups), benzyloxycarbonyl groups such as benzyloxycarbonyl, o-bromobenzyloxycarbonyl, o- or p-chlorobenzyloxycarbonyl, p-nitrobenzyloxycarbonyl, p-methoxybenzyloxycarbonyl, p-phenylazo-benzyloxycarbonyl or p-(p'-methoxyphenylazo)-benzyloxycarbonyl, aliphatic oxycarbonyl groups such as cyclopentyloxycarbonyl, trichloroethyloxycarbonyl, t-amyloxycarbonyl, t-butoxycarbonyl or diisopropylmethoxycarbonyl, and aralkyloxycarbonyl groups such as 2-phenyl-isopropoxycarbonyl, 2-tolylisopropoxycarbonyl or 2-p-diphenyl-isopropoxycarbonyl. Amino groups can also be protected by enamine formation by reaction with a 1,3-diketone such as benzoylacetone, acetylacetone or dimedone. Carboxyl groups can be protected by amide formation, hydrazide formation or esterification. Amide groups are substituted with 3,4-dimethoxybenzyl, bis-(p-methoxyphenyl)-methyl or like groups. Hydrazide groups are substituted with benzyl oxycarbonyl, trichloroethyloxycarbonyl, trifluoroacetyl, t-butoxycarbonyl, trityl or 2-p-diphenyl-isopropoxycarbonyl. Ester groups are substituted with alkanols such as methanol, ethanol, t-butanol or cyanomethylalcohol, aralkanols such as benzyl alcohol, p-bromobenzyl alcohol, p-chlorobenzyl alcohol, p-methoxybenzyl alcohol, p-nitrobenzyl alcohol, 2,4,6-trimethylbenzyl alcohol, benzhydryl alcohol, benzoylmethyl alcohol, p-bromobenzoylmethyl alcohol or p-chlorobenzoylmethyl alcohol, phenols such as 2,4,6-trichlorophenol, 2,4,5-trichlorophenol, pentachlorophenol, p-nitrophenol, 2,4-dinitrophenol, p-cyanophenol or p-methansulfonylphenol and thiophenols such as thiophenol, thiocresol or p-nitrothiophenol.

Hydroxyl groups can be protected by esterification or etherification. Examples of groups for esterification are lower alkanoyl groups such as acetyl, aroyl groups such as benzoyl or groups derived from benzyloxycarbonyl or ethyloxycarbonyl. Examples of groups for etherification are, for example, benzyl, tetrahydropyranyl or t-butyl. Further preferred examples of protective groups for hydroxyl groups are 2,2,2-trifluoro-1-t-butyloxycarbonylamino ethyl and 2,2,2-trifluoro-1-benzyloxycarbonylamino ethyl. Hydroxyl groups need not always be protected. Protective groups for imino groups can for example be benzyl, trityl, benzyloxycarbonyl, tosyl, adamantyloxycarbonyl, 2,2,2-trifluoro-1-t-butyloxycarbonylamino ethyl or 2,2,2-trifluoro-1-benzyloxycarbonylamino ethyl. Imino groups also need not always be protected.

Thiolcarboxylic acids comprising condensation products of amino acids or lower peptides of 2-4 amino acids can be prepared by reacting amino acids of peptides which have protected α-amino groups and activated terminal carboxyl groups with amino acids or peptides which have free α-amino groups and protected terminal carboxyl groups, or by reacting amino acids or peptides which have activated α-amino groups and protected terminal carboxyl groups with amino acids or peptides which have free terminal carboxyl groups and protected α-amino groups.

A compound of the formula [II]

$$R_1\text{—S—S—}R_1 \qquad [II]$$

is reacted with a compound of the formula [III]

$$HS\text{—}R_2\text{-(-CO—}R_3\text{-)}_n R_5 \qquad [III]$$

usually in a solvent such as methanol, ethanol, acetone, benzene, chloroform or carbon tetrachloride.

To the solvent is added each compound in equimolar ratio and the mixture is reacted at 10°–70° C., preferably at 70° C., for 10 minutes to 5 hours, preferably for 2–3 hours.

After reaction the product of the formula [IV]

$$R_1\text{—S—S—}R_2\text{-(-CO—}R_3\text{-)}_n R_5 \qquad [IV]$$

is obtained in any usual way such as cooling and extraction.

In the said product, the carboxyl groups can remain as is, or carboxyl or nitrile groups are conventionally changed to reactive derivatives of carboxyl groups or protected carboxyl groups, and also nitrile groups are changed to imidate groups to obtain the product of formula [I].

Examples of reactive derivatives of carboxyl groups are conventional derivatives such as acid azides, acid anhydrides, acid imidazolides, active esters or acid halogenides, for example cyanomethyl ester, thiophenyl ester, p-nitrothiophenyl ester, p-methanesulfonylphenyl ester, thiodyl ester, p-nitrophenyl ester, 2,4-dinitrophenyl ester, 2,4,5-trichlorophenyl ester, 2,4,6-trichlorophenyl ester, pentachlorophenyl ester, N-hydroxysuccinimide ester, N-hydroxyphthalimide ester, 8-hydroxyquinoline ester or N-hydroxypiperidine ester. Further reactive derivatives can be obtained by using carbodiimide, N,N'-carbonyl diimidazole or isoxazolium such as Woodward reagent.

In Table 2, some examples of disulfide compounds of the present invention compared with 3-(pyridine-2'-yl-dithio)propionic acid are illustrated. S—S exchange reaction rates were measured by reaction with dithiothritol containing 1 mM EDTA in 0.2 M tris-HCl buffer (pH 7.5) as a compound having a thiol group; and subsequently increased absorbency was measured at its maximum absorbency wave length to determine the molar ratio of S—S exchange reaction per minute.

As illustrated in the table, the disulfide derivatives of the present invention have a higher S—S exchange reaction rate.

having a hydroxyl group or an amine compound. Subsequently the disulfide bond of the compound is hydrolyzed to introduce the thiol group into the compound having a hydroxyl group or the amino compound. Also the above compound with an ester or amide linkage is reacted with a compound having a thiol group, in aqueous medium at pH 7-8 to effect the S—S exchange

| | | $R_1-S-S-R_2(CO-R_3)_nR_4$ | | | | S—S exchange reaction rate | |
|---|---|---|---|---|---|---|---|
| $R_1$ | $R_2$ | $-(COR_3)-$ | n | $R_4$ | substance measured | wave length measured | reaction rate $\mu$ mole /min. |
| The present invention | | | | | | | |
| benzothiazol-2-yl | $-CH_2-CH_2-$ | | 0 | $-COOH$ | benzothiazol-2-yl-SH | 310 nm | 39.0 |
| " | $-CH(CH_3)-$ | | 0 | $-COOH$ | " | " | 37.4 |
| " | $-CH_2 \cdot CH_2-$ | | 0 | $-COO-C_6H_4-NO_2$ | " | " | 35.7 |
| " | $-CH_2 \cdot CH_2-$ | $-CONHCH_2(CH_2)_3CH_2-$ | 1 | $-COOH$ | " | " | 34.3 |
| " | $-CH_2 \cdot CH(NH_2)-$ | | 0 | $-COOH$ | " | " | 35.6 |
| " | $-C(CH_3)_2-CH(NH_2)-$ | | 0 | $-COOH$ | " | " | 35.0 |
| " | $-CH(CH_2COOH)-$ | | 0 | $-COOH$ | " | " | 36.2 |
| " | $-CH(COOH) \cdot CH_2-$ | | | | | | |
| pyridyl-N-oxide | $-CH_2 \cdot CH_2-$ | | 0 | $-COOH$ | pyridyl-N-oxide-SH | 333 nm | 93.6 |
| " | $-CH_2-CH_2-$ | | 0 | $-COO-C_6H_4-NO_2$ | " | " | 93.5 |
| " | $-CH_2 \cdot CH(NH_2)-$ | | 0 | $-COOH$ | " | " | 90.3 |
| " | $-C(CH_3)_2-CH(NH_2)-$ | | 0 | $-COOH$ | " | " | 91.6 |
| controle | | | | | | | |
| pyridyl | $-CH_2-CH_2-$ | | 0 | $-COOH$ | 2-thiopyridone | 343 nm | 8.7 |

The disulfide derivatives [I] are useful as thiol group introducing reagents and cross linking reagents. For example, disulfide derivative [I] can be reacted with a compound having reactive hydrogen groups as amine compounds, in a solvent such as benzene, toluene, chloroform, acetone, tetrahydrofuran or dimethylformamide in the optional presence of a condensation reagent to form esters, or amidino or amide linkages, by reacting the reactive group $R_4$ of the disulfide derivative with the hydroxyl group or amino group in a compound reaction, thereby cross linking the compound having thiol groups and the compound having hydroxyl groups or the amine compound.

Examples of such compounds having hydroxyl groups or amine compounds are insulin, albumin, growth hormone, calcitonin, prolactin, ACTH, PTH, glucagon, gastricsin, secretin, γ-globulin, or immune components such as IgG, IgM, IgA, secondary antibodies, estrogen, ATP, catecholamine, triiodothyronine;

antigents of antibiotics or hypnotics, antibodies, secondary antibodies and hapten; or oxido-reductases such as peroxidase, catalase, cholesterol oxidase, glyceroldehydrogenase or choline oxidase, hydrolases such as alkaline phosphatase, glucoamylase, phospholipase D, β-galactosidase or lysozyme or other transferases, lyase, isomerase, polysaccharides such as cellulose, aminated cellulose, agarose, dextrine, dextran or their water insoluble carriers, or water insoluble carriers having hydroxyl or amino groups such as aminated polyamides, polyacrylonitriles or silanes. Also the carriers include either known compounds or novel compounds which can be used as carriers in the present invention. Examples of novel compounds having amino groups are γ-aminopropylated polyamides, amino derivatives of polyacrylonitrile polymers or polyacrylonitrile group polymers. A γ-aminopropylated polyamide is prepared by heating a polyamide carrier such as 6,6-nylon and 6-nylon in γ-aminopropyl triethoxysilane at 100° C. for three hours to introduce partially γ-aminopropyl groups into the amide groups of the polyamide compound. The amino derivatives of polyacrylonitrile polymers or polyacrylonitrile group polymers can be prepared by heat-refluxing a polyacrylonitrile polymer or polyacrylonitrile group polymer in the presence of lithium aluminum hydride in a medium such as diethyl ether, dioxane or tetrahydrofuran for 1–48 hours to form amino groups with partially reduced nitrile groups.

Examples of compounds having a thiol group are for example enzymes such as peroxidase, catalase, β-galactosidase or alkaline phosphatase or hapten, or compounds into which a thiol group has been introduced by S-acetylmercaptosuccinic anhydride [Arch. Biochem. Biophys., 96, 605–612 (1962)], or a thiol group-introduced compound having hydroxyl groups prepared by hydrolysis of disulfide derivative [I] or an amine compound.

The S—S exchange reaction is performed, as hereinbefore explained, by optionally combining the above compounds conventionally in an aqueous medium such as one buffered at pH 7–8 at room temperature. The reaction product is recovered by conventional separation and purification methods such as salting out, phase separation, extraction, dialysis or adsorption chromatography. The thus-produced compound is an advantageous and useful compound for immobilizing enzymes, cross linking enzymes and water-insoluble carriers, for immobilizing antigens or antibodies, cross linking antigens or antibodies and water-insoluble carriers, for antigenic haptens, cross linking proteins and haptens, or, as enzyme immuno assay components, the cross linking of enzymes and immune components.

The following examples non-limitatively illustrate the present invention.

EXAMPLE 1

To 2,2'-dithio-bis-(benzothiazole) (13.2 g) is added benzene (400 ml) and 3-mercaptopropionate (6 g), and the mixture is reacted at 70° C. for 3 hours with stirring. Thereafter the reaction mixture is cooled in an ice bath to precipitate the crude crystals (13.8 g) which are recrystallized from benzene to obtain 3-(benzothiazol-2'-yl-dithio) propionate crystals (12 g)

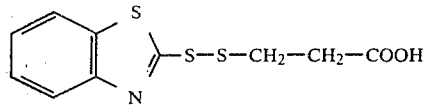

m.p. 162°–164° C.
λmax: 272 nm (methanol)
Rf: 0.33 (TLC, silica gel, benzene:ethyl acetate=1:2).

EXAMPLE 2

2,2'-dithio-bis (pyridine-N-oxide) (4.3 g) is added to chloroform (200 ml) and 3-mercaptopropionate (3 g) and the mixture is reacted at 70° C. for 3 hours. The reaction mixture is cooled, and the crude crystals precipitate and are recrystallized from chloroform to obtain crystals of 3-(pyridine-N-oxide-2'-yl-dithio) propionate (4.1 g).

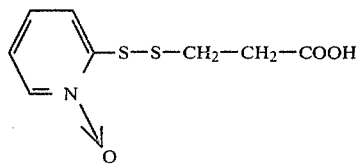

m.p. 126°–218° C.
λmax: 270 nm (methanol)
Rf: 0.66 (TLC, silica gel, butanol:acetic acid:water=4:1:1).

EXAMPLE 3

To 3-(benzothiazole-2'-yl-dithio)-propionate (3 g) in ethyl acetate (20 ml) are added N-hydroxysuccinimide (1 gl) and dicyclohexylcarbodiimide (1.7 g), and the mixture is stirred at ambient temperature for 3 hours. The precipitated dicyclohexylurea is filtered off and the filtrate is washed with phosphate buffer (pH 7.5 ) to remove unreacted free acid. The ethyl acetate layer is dehydrated by adding anhydrous sodium sulfate, and dried and recrystallized from hot petroleum ether to obtain crystals of 3-(benzothiazole-2'-yl-dithio) propionate succinimide ester (2.4 g)

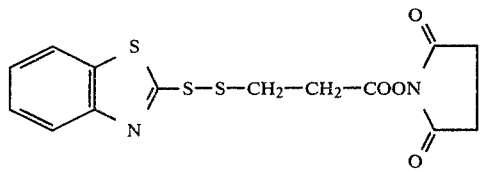

m.p. 114°–115° C., corrected value: 121°–123° C.
λmax: 270 nm (pH 7.5, 10% aqueous dimethylformamide)
Rf: 0.53 (TLC, silica gel, benzene: ethyl acetate=3:1).

EXAMPLE 4

A mixture of 3-(benzothiazole-2'-yl-dithio) propionate (3 g) obtained by the same preparation process as described in Example 1, and p-nitrophenol (1.2 g) and dicyclohexylcarbodiimide (2.1 g), dissolved in ethyl acetate (20 ml), is stirred at room temperature for 3 hours. The remaining procedure is carried out as in Example 3 to obtain 3-(benzothiazole-2'-yl-dithio) propionate p-nitrophenyl ester (1.85 g) as crystals

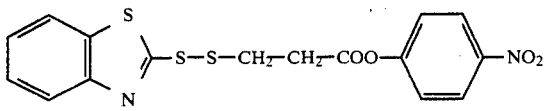

m.p. 113°–114° C.
λmax: 279 nm (pH 7.5, 10% aqueous dimethylformamide)
Rf: 0.84(TLC, silica gel, benzene:ethyl acetate=5:1)

EXAMPLE 5

3-(benzothiazole-2'-yl-dithio) propionate (3 g) dissolved in thionyl chloride (10 ml) is reacted at 25° C. for 2 hours, thereafter thionyl chloride is removed in vacuo to obtain 3-(benzothiazole-2'-yl-dithio) propionyl chloride as, an oily substance.

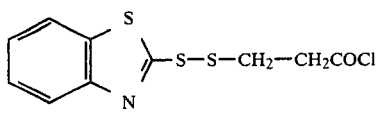

λmax=272 nm (methanol)
Rf=0.25 (TLC, benzene)

EXAMPLES 6 and 7

3-(benzothiazole-2'-yl-dithio) propionate succinimide ester (1.3 g) prepared by the same procedure as in Example 3 and ε-aminocaproic acid (0.6 g) are added to tetrahydrofuran (50 ml), and the mixture is reacted at room temperature overnight; the tetrahydrofuran is removed in vacuo, and the medium is thereafter dissolved in hot isopropanol and cooled to obtain crystals of 6-N-[3-(benzothiazole-2'-yl-dithio) propionyl]aminohexanoic acid (0.8 g)

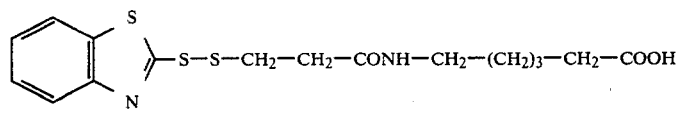

λmax=272 nm (in methanol)
Rf=0.07 (TLC silica gel, benzene:ethyl acetate=1:2).

The above-obtained compound (500 mg), N-hydroxysuccinimide (200 mg) and dicyclohexylcarbodiimide (340 mg) dissolved in tetrahydrofuran (10 ml) are reacted at room temperature for 3 hours; the precipitated dicyclohexylurea is filtered off and the tetrahydrofuran is distilled off. The residue is dissolved in hot petroleum ether and cooled to obtain crystals of 6-N-[3-(benzothiazole-2'-yl-dithio)-propionyl]aminohexanate succinimide ester (430 mg)

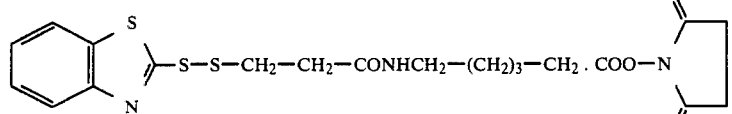

λmax: 271 nm

Rf: 0.42 (TLC, silica gel, benzene:ethyl acetate=3:1).

EXAMPLES 8, 9 and 10

3-(pyridine-N-oxide-2'-yl-dithio) propionate obtained by the same process as in Example 2 was used to prepare succinimide ester, p-nitrophenyl ester and acid chloride thereof according to the method of Examples 3, 4 and 5, respectively.

Succinimide ester:

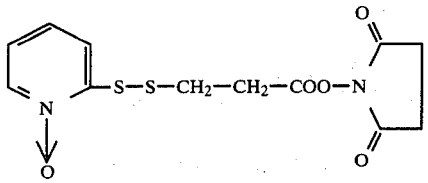

λmax: 260 nm (methanol)
Rf: 0.25 (TLC, silica gel, benzene:ethyl acetate=3:1).
p-nitrophenyl ester:

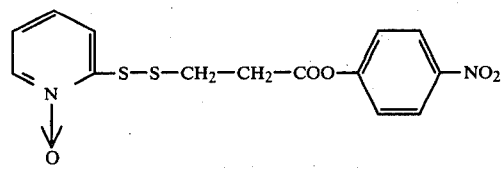

λmax: 391 nm (methanol)
Rf: 0.82 (TLC, silica gel, benzene:ethyl acetate=3:1).
Acid chloride:

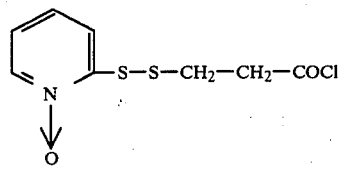

λmax: 270 nm (methanol)
Rf: 0.15 (TLC, silica gel, benzene:ethyl acetate=3:1).

EXAMPLE 11

2,2'-dithio-bis (benzothiazole) (1.1 g) and 3-mercaptopropionitrile dissolved in benzene (50 ml) are reacted at 70° C. for 3 hours with stirring. The reaction mixture is cooled in an ice water bath to precipitate the crude crystals which are recrystallized from benzene to obtain 3-(benzothiazole-2'-yl-dithio) propionitrile (750 mg).

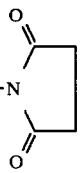

700 mg thereof is added to a methanol solution (50 ml)

containing HCl (19 g) and reacted at 5° C. for overnight, and the solvent is distilled off in vacuo to obtain a crude powder which is washed with benzene to yield methyl 3-(benzothiazole-2'-yl-dithio) propionimidate hydrochloride (720 mg)

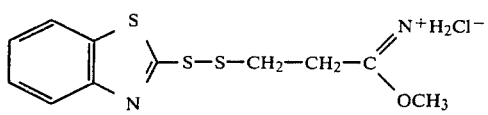

λmax=272 nm (methanol)
Rf=0.05 (TLC, silica gel, benzene:ethyl acetate=1:2).

EXAMPLES 12-35

2,2'-dithio-bis (benzothiazole) or 2,2'-dithio-bis (pyridine-N-oxide) as prepared hereinbefore is used together with thioglycolic acid, thiolactic acid, cysteine, thiomalic acid, penicillamine, N-(2-mercaptopropionyl)-glycine or glutathione under the same reaction conditions as hereinbefore and the following compounds are obtained. In the examples, Rf values are given for silica gel thin layer chromatography.

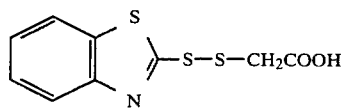 (12)

λmax=272 nm (methanol)
Rf=0.36 (benzene:methanol=1:2)
S—S exchange reaction rate: 35.6 μmoles/min.

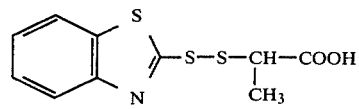 (13)

λmax: 272 nm
Rf: 0.38 (benzene:methanol=1:2

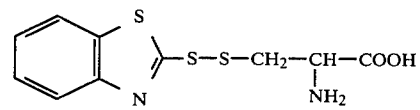 (14)

λmax: 271 nm (methanol)
Rf: 0.08 (benzene:methanol=1:2); 0.60 (upper layer; butanol:acetic acid:water=4:1:5).

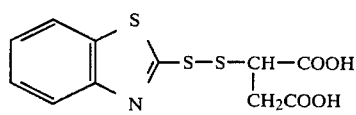 (15)

λmax: 271 nm (methanol)
Rf: 0.15 (benzene:ethyl acetate=1:2).

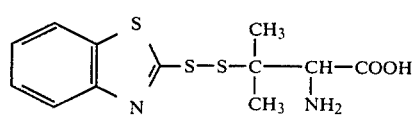 (16)

λmax: 271 nm (pH 7.5, phosphate buffer)
Rf: 0.60 (butanol:acetic acid:water=4:1:5 upper layer).

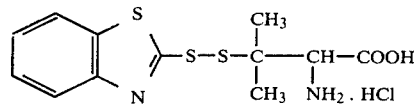 (17)

λmax: 271 nm (methanol)
Rf: 0.30 (upper layer; butanol:acetic acid:water=4:1:5)
S—S exchange reaction rate:35.5 μmoles/min.).

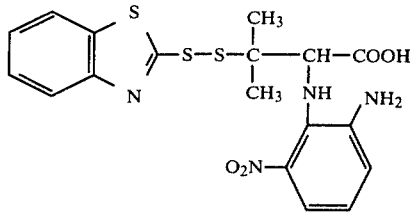 (18)

λmax: 271 nm, 418 nm (methanol)
Rf: 0.23 (upper layer; butanol:acetic acid:water=4:1:5).

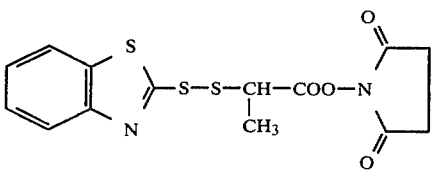 (19)

λmax: 271 nm (methanol)
Rf: 0.48 (benzene:ethyl acetate=3:1).

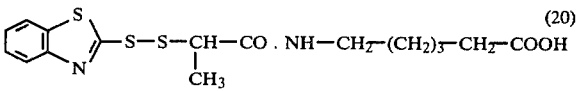 (20)

λmax: 271 nm (methanol)
Rf: 0.12 (benzene:ethyl acetate=3:1)
S—S exchange reaction rate: 35.0 μmoles/min.

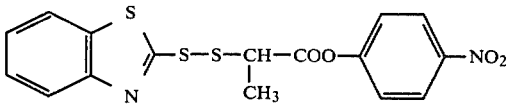 (21)

λmax: 278 nm
Rf: 0.80 (benzene:ethyl acetate=3:1).

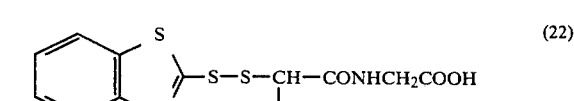 (22)

λmax: 271 nm (methanol)
Rf: 0.15 (benzene:ethyl acetate=3:1)
S—S exchange reaction rate: 36.6 μmoles/min.

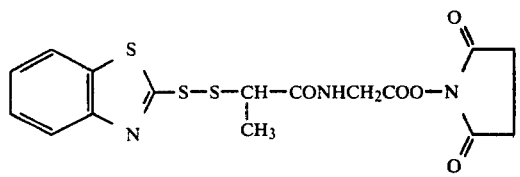
(23)

λmax: 271 nm (methanol)
Rf: 0.80 (benzene:ethyl acetate=3:1).

(24)

λmax: 271 nm (methanol)
Rf: 0.10 (benzene:ethyl acetate=3:1)
S—S exchange reaction rate: 35.7 μmoles/min.

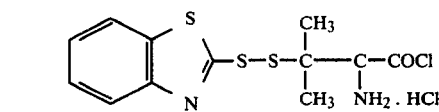
(25)

λmax: 271 nm (methanol)
Rf: 0.05 (benzene:ethyl acetate=3:1).

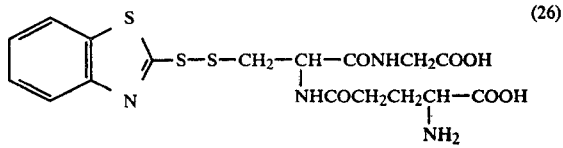
(26)

λmax: 272 nm (methanol)
Rf: 0.31 (upper layer; butanol:acetic acid:water=4:1:5)
S—S exchange reaction rate: 35.2 μmoles/min.

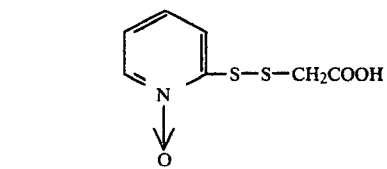
(27)

λmax: 270 nm (methanol)
Rf: 0.7 (upper layer; butanol:acetic acid:water=4:1:1)
S—S exchange reaction rate: 92.8 μmoles/min.

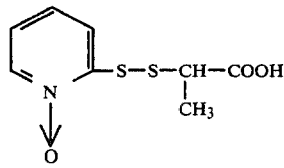
(28)

λmax: 270 nm (methanol)
Rf: 0.66 (butanol:acetic acid:water=4:1:1, upper layer)
S—S exchange reaction rate: 93.2 μmoles/min.

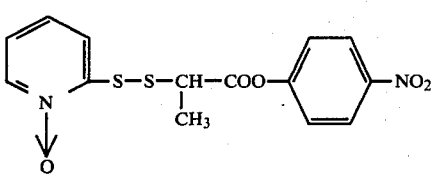
(29)

λmax: 310 nm (methanol)
Rf: 0.82 (benzene:ethyl acetate=3:1).

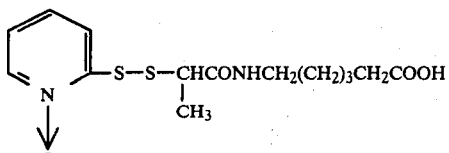
(30)

λmax: 271 nm (methanol)
Rf: 0.41 (butanol:acetic acid:water=4:1:1)
S—S exchange reaction rate: 92.6 μmoles/min.

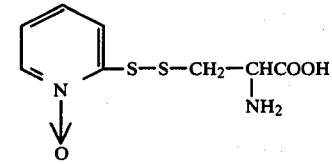
(31)

λmax: 271 nm (methanol)
Rf: 0.25 (butanol:acetic acid:water=4:1:1).

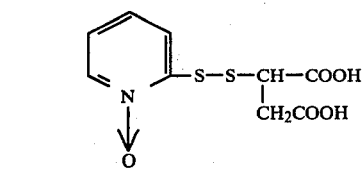
(32)

λmax: 270 nm (methanol)
Rf: 0.32 (butanol:acetic acid:water=4:1:1:)
S—S exchange reaction rate: 90.1 μmoles/min.

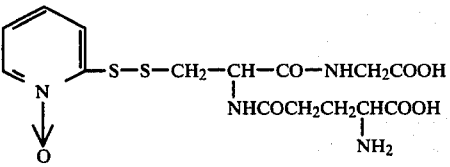
(33)

λmax: 270 nm
Rf: 0.20 (butanol:acetic acid:water=4:1:1)
S—S exchange reaction rate: 91.5 μmoles/min.

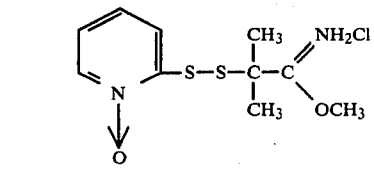
(34)

λmax: 270 nm

Rf: 0.41 (butanol:acetic acid:water=4:1:1).

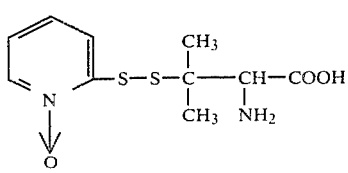

(35)

λmax: 270 nm

Rf: 0.25 (butanol:acetic acid:water=4:1:1).

Example 36

To a bovine insulin (0.6 mg) dissolved in 0.1 M veronal buffer (pH 7.5, 10 ml) was added dimethylformamide solution (1 ml) of 3-(benzothiazole-2′-yl-dithio) propionate succinimide ester (3.1 mg), and the mixture was stirred for 4 hours at room temperature. Thereafter the reaction mixture was adjusted to pH 5.0 to precipitate the product, which was centrifuged at 3000 r.p.m. for 10 minutes to obtain an insulin derivative with the introduced 3-(benzothiazole-2′-yl-dithio) propionitrile group.

This insulin derivative was washed with citrate buffer (pH 5) and dissolved in 0.1 M phosphate buffer (10 ml, pH 7.5).

To the resulting solution (0.1 ml) was added β-galactosidase (5 mg) dissolved in phosphate buffer (pH 7.5, 5 ml) and the mixture was allowed to react at room temperature for one hour. Thereafter the reaction mixture was charged on a column of Sephadex G-100 (trade name, 1×80 cm), eluted with 0.01 M phosphate buffer (pH 7.5) containing 0.15 M NaCl and the 4 ml fractions were collected. Fractions Nos. 7-8 were collected to obtain cross-linked compounds of insulin and β-galactosidase.

To 0.02 ng-10 ng of bovine insulin in test tubes were added the cross-linked compounds of insuline and β-galactosidase hereinabove and anti-bovine insulin serum, and the mixtures were incubated at 5° C. overnight and further incubated at 5° C. overnight with the addition of rabbit anti-guinea pig IgG gerum as secondary antibody. The incubation mixture was centrifuged at 3000 r.p.m. for 10 minutes and the thus-obtained precipitate was incubated at 44° C. for 20 minutes by β-galactosidase colorimetry with the addition of 200 μl of o-nitrophenylgalactoside (5 mg/ml, 0.1% bovine serum albumin, 10 mM mercaptoethanol in 0.1 M phosphate buffer, pH 6.7). Subsequently the reaction was stopped by adding glycine buffer (pH 10.5, 0.1 M, 25 ml) and the product was colorimetrically assayed at 420 nm to measure the β-galactosidase activity. Thus was effected the enzyme immuno assay of insulin using insulin-β-galactosidase cross-linkage compound, anti-insulin serum and secondary antibody. The results are shown in the accompanying drawing, in which a good linear relationship is apparent.

EXAMPLE 37

Bovine insulin in Example 36 hereinabove was replaced by guinea pig anti-bovine serum which was reacted with 3-(benzothiazole-2′-yl-dithio) propionate succinimide ester to obtain guinea pig anti-bovine insulin-β-galactosidase cross-linked compound.

EXAMPLE 38

To β-galactosidase (5 mg) in 0.1 M veronal buffer (5 ml, pH 7.5 (was added 3-(benzothiazole-2′-yl-dithio) propionate succinimide ester (3.1 mg) in dimethylformamide (1 ml), and the mixture was stirred at room temperature for 4 hours to obtain 3-(benzothiazole-2′-yl-dithio) propionated β-galactosidase which was subsequently added to an aqueous medium adjusted to pH 9.0 by addition of 0.1 N sodium carbonate. The mixture was allowed to stand for 2 hours. The resulting S—S bonds thereof were hydrolyzed to obtain β-thiopropionated β-galactosidase (20 β-thiopropionyl groups were introduced per β-galactosidase molecule).

What is claimed is:

1. A disulfide derivative selected from the group consisting of

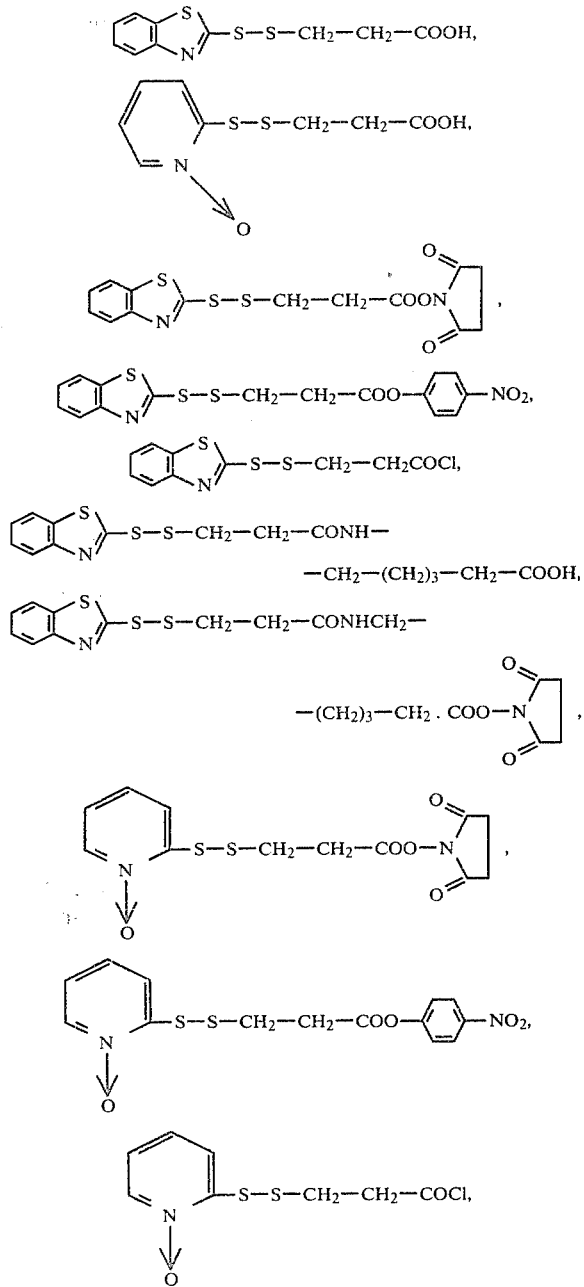

-continued
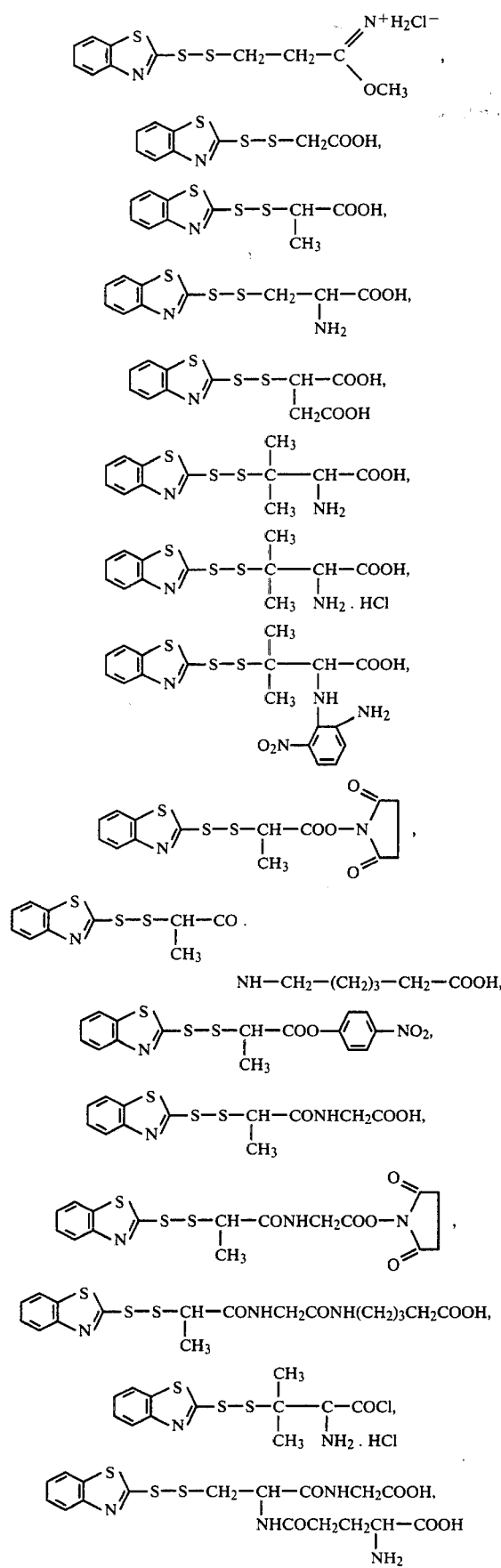
-continued
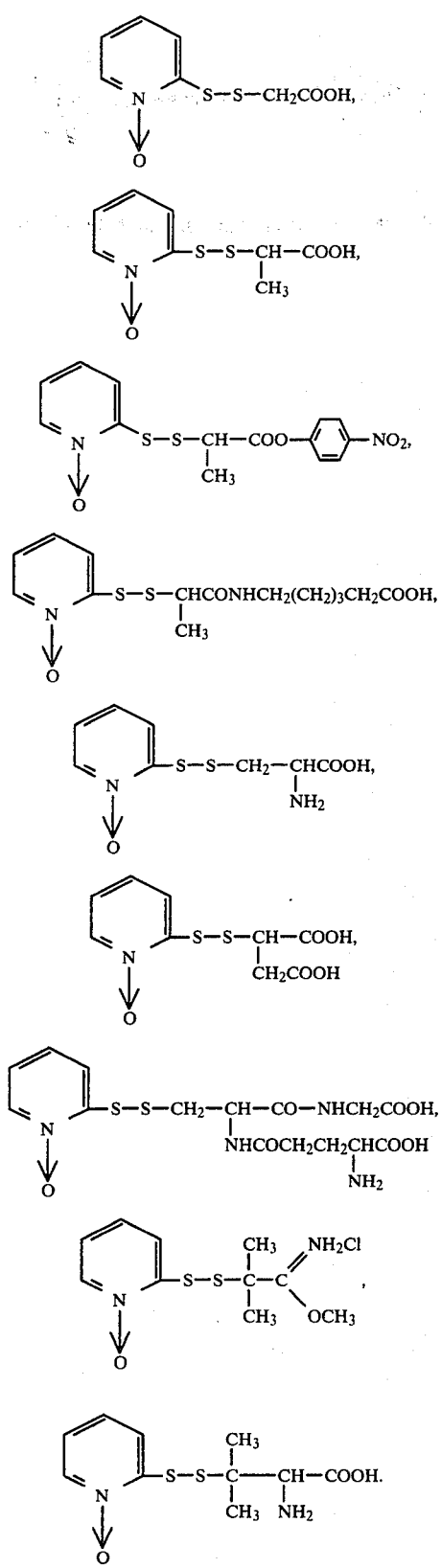
and
2. A derivative as claimed in claim 1, in which said member is 3. A derivative as claimed in claim 1, in which said member is
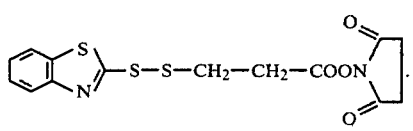
4. A derivative as claimed in claim 1, in which said member is
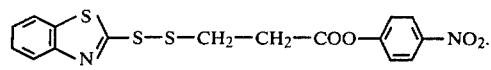
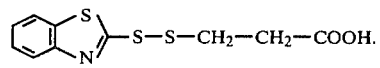
* * * * *